United States Patent
Zhang

(10) Patent No.: US 11,325,976 B2
(45) Date of Patent: May 10, 2022

(54) ANTI-PROGRAMMED DEATH-LIGAND 1 (PD-L1) ANTIBODIES AND THERAPEUTIC USES THEREOF

(71) Applicants: Ying Zhang, Hunan (CN); Xiangtan Tenghua Bioscience, Hunan (CN)

(72) Inventor: Ying Zhang, Hunan (CN)

(73) Assignees: Ying Zhang, Hunan (CN); XIANGTAN TENGHUA BIOSCIENCE, Hunan (CN)

( * ) Notice: Subject to any disclaimer, the term of this patent is extended or adjusted under 35 U.S.C. 154(b) by 200 days.

(21) Appl. No.: 16/486,150

(22) PCT Filed: Feb. 16, 2017

(86) PCT No.: PCT/IB2017/050855
§ 371 (c)(1),
(2) Date: Aug. 14, 2019

(87) PCT Pub. No.: WO2018/150224
PCT Pub. Date: Aug. 23, 2018

(65) Prior Publication Data
US 2020/0165340 A1 May 28, 2020

(51) Int. Cl.
*C07K 16/28* (2006.01)
*A61P 35/00* (2006.01)
*A61K 31/454* (2006.01)
*A61K 39/395* (2006.01)
*A61K 39/00* (2006.01)

(52) U.S. Cl.
CPC ........ *C07K 16/2827* (2013.01); *A61K 31/454* (2013.01); *A61K 39/3955* (2013.01); *A61P 35/00* (2018.01); *A61K 2039/505* (2013.01); *C07K 2317/565* (2013.01); *C07K 2317/732* (2013.01); *C07K 2317/734* (2013.01)

(58) Field of Classification Search
CPC .......... C07K 16/2827; C07K 2317/734; A61K 31/454; A61K 2039/505
See application file for complete search history.

(56) References Cited

U.S. PATENT DOCUMENTS 8,217,149 B2  7/2012  Irving et al.

FOREIGN PATENT DOCUMENTS

| CN | 104673897 A | 6/2015 |
|---|---|---|
| CN | 105968200 A | 9/2016 |
| CN | 106103482 A | 11/2016 |
| CN | 106243225 A | 12/2016 |
| WO | WO-2007/005874 A2 | 1/2007 |
| WO | WO-2010/077634 A1 | 7/2010 |
| WO | WO-2011/066342 A2 | 6/2011 |
| WO | WO-2011/066389 A1 | 6/2011 |
| WO | WO-2013/173223 A1 | 11/2013 |
| WO | WO-2014/100079 A1 | 6/2014 |

OTHER PUBLICATIONS

Almagro & Fransson, Humanization of antibodies, Frontiers in Bioscience 2008; 13: 1619-33 (Year: 2008).*
Brahmer, et al. "Safety and Activity of Anti-PD-L1 Antibody in Patients with Advanced Cancer", N Engl J Med. 2012;366(26):2455-65.
Keir, et al., "PD-1 and its ligands in tolerance and immunity", Annu Rev Immunol. 2008;26:677-704.
Massard, et al., "Safety and Efficacy of Durvalumab (MEDI4736), an Anti-Programmed Cell Death Ligand-1 Immune Checkpoint Inhibitor, in Patients With Advanced Urothelial Bladder Cancer", J Clin Oncol , 2016, 34, 9761.
Powles, et al: "MPDL3280A (anti-PD-L1 ) treatment leads to clinical activity in metastatic bladder cancer", Nature, 2014, 515:558-562.
Velcheti, et al. "Programmed death ligand-1 expression in non-small cell lung cancer", Lab Invest. 2014;94:107-16.
Webster, "The immune checkpoint inhibitors: where are we now?", Nat Rev Drug Discov. 2014;13(12):883-4.

* cited by examiner

*Primary Examiner* — Peter J Reddig
*Assistant Examiner* — Cheng Lu
(74) *Attorney, Agent, or Firm* — Ballard Spahr LLP

(57) ABSTRACT

Anti-programmed death-ligand 1 (PD-L1) antibodies, methods of using the same, therapeutic compositions thereof, and uses thereof in upregulating cell-mediated immune responses and treating T cell dysfunctional disorders are provided. The use of the anti-PD-L1 antibody as a diagnostic agent in vitro is also provided.

8 Claims, 9 Drawing Sheets
Specification includes a Sequence Listing.

ANTI-PROGRAMMED DEATH-LIGAND 1 (PD-L1) ANTIBODIES AND THERAPEUTIC USES THEREOF

CROSS REFERENCE TO RELATED APPLICATION

This application claims the benefit of priority under 35 U.S.C. § 371 of International Application No. PCT/IB2017/050855, filed on Feb. 16, 2017. The content of this earlier filed application is hereby incorporated by reference herein in its entirety.

SEQUENCE LISTING

The sequence listing submitted Aug. 14, 2019 as a text file named "13318_0044U1_Sequence Listing," created on Aug. 12, 2019, and having a size of 8,170 bytes, is hereby incorporated by reference pursuant to 37 C.F.R. § 1.52(e)(5).

TECHNICAL FIELD

The present invention relates to antibody or functional binding fragments that binds programmed cell death-ligand 1 (PD-L1) and particularly for therapeutic and diagnostic methods of using those antibodies. The present invention belongs to the field of biotechnology

BACKGROUND ART

PD-L1 is a 40 kDa type I transmembrane protein that has been speculated to play a major role in suppressing the immune system. Formation of the PD-L1/PD-1 and PD-L1/B7.1 complexes negatively regulates T-cell receptor signaling, resulting in the subsequent downregulation of T cell activation and suppression of anti-tumor immune activity.

PD-L1 regulates the immune response in the suppression of immune system responses during chronic infections, pregnancy, tissue allografts, autoimmune diseases, and cancer.

PD-L1 binds to its receptor, PD-1, found on activated T cells, B cells, monocytes and myeloid cells, to modulate activation or inhibition. PD-L1 also has an appreciable affinity for the costimulatory molecule CD80 (B7-1).

Engagement of PD-L1 with its receptor PD-1 on T cells delivers a signal that inhibits TCR-mediated activation of IL-2 production and T cell proliferation. The mechanism involves inhibition of ZAP70 phosphorylation and its association with CD3ζ. PD-L1 binding to PD-1 also contributes to ligand-induced TCR down-modulation during antigen presentation to naive T cells, by inducing the up-regulation of the E3 ubiquitin ligase CBL-b.

PD-L1 is overexpressed in many cancers, including a wide variety of solid tumors and hematological malignances, such as myeloma, prostate, breast, colon, lung, melanoma, ovarian, salivary, stomach, thyroid tumors, lymphoma and bladder. PD-L1 overexpression in tumor cells may advance tumor invasion and is often associated with poor prognosis.

Furthermore, in many cancers, PD-L1 is over expressed on tumor cells and tumor-infiltrating immune cells, such as macrophages and dendritic cells.

Given the role of PD-L1 in cancer development and immune system regulation, additional tools to detect the presence of PD-L1, for example for diagnosis and/or patient selection, are desirable.

The blockade therapy of PD-L1 target shows promising clinical benefits in many types of cancer. There is a need in the art for agents that target PD-L1 for the treatment of PD-L1-associated conditions, such as cancer. The invention fulfills that need and provides other benefits.

Monoclonal antibodies to PD-L1 are known in the art and have been described, for example, in US Patent/Publication Nos. U.S. Pat. No. 8,217,149, US20130309250, US20160009805, U.S. Pat. No. 7,943,743B2 and WO Patent/Publication Nos. WO2007005874A2, WO2010077634A1, WO2011066342A2, WO2011066389A1, WO2014100079A1, WO2013173223A1.

SUMMARY OF INVENTION

The present invention relates to anti-PD-L1 antibodies and methods of using the same.

The present disclosure provides antibodies that can act as agonists and/or antagonists of PD-L1, thereby modulating immune responses regulated by PD-L1. The disclosure further provides anti-PD-1 antibodies that comprise novel antigen-binding fragments. Anti-PD-L1 antibodies of the invention are capable of:

(A) Specifically binding to PD-L1, including human PD-L1;

(B) Blocking PD-L1 interactions with its natural ligand(s);

(C) Increasing T-cell proliferation in a mixed lymphocyte reaction (MLR);

(D) Killing cancer cell by cytotoxic T lymphocyte (CTL);

(E) Killing cancer cell by antibody dependent cell-mediated cytotoxicity (ADCC);

(F) Killing cancer cell by complement dependent cytotoxicity (CDC);

(G) Killing myeloma cancer cell and prolongs survive rate in NSG mice;

(H) Killing myeloma cancer cell and prolongs survive rate in SCID lymphoma mice; or (I) Performing all functions above.

In particular embodiments, the two antibodies derived and defined from mouse comprise a heavy chain variable region ($V_H$) and/or a light chain variable region ($V_L$) and their Complementarity Determining Region (CDR) as summarized in Table below:

Part A. A full variable sequence of PD-L1 antibodies derived from mouse

| Antibody | Variable Region | SEQ ID NO | Sequence Type |
|---|---|---|---|
| Q106 | Heavy Chian ($V_H$) | 1 | DNA |
|  | Heavy Chian ($V_H$) | 2 | Protein |
|  | Light Chian ($V_L$) | 3 | DNA |
|  | Light Chian ($V_L$) | 4 | Protein |

| Q107 | Heavy Chian (V$_H$) | 5 | DNA |
| | Heavy Chian (V$_H$) | 6 | Protein |
| | Light Chian (V$_L$) | 7 | DNA |
| | Light Chian (V$_L$) | 8 | Protein |

| Part B. CDR domain sequence of PD-L1 antibodies derived from mouse | | | | | | |
|---|---|---|---|---|---|---|
| | | Complementarity Determining Region | | | SEQ ID | Sequence |
| Antibody | | CDR1 | CDR2 | CDR3 | NO | Type |
| Q106 | V$_H$ | CDR-H1 | CDR-H2 | CDR-H3 | 9-11 | Protein |
| | V$_L$ | CDR-L1 | CDR-L2 | CDR-L3 | 12-14 | Protein |
| Q107 | V$_H$ | CDR-H1 | CDR-H2 | CDR-H3 | 15-17 | Protein |
| | V$_L$ | CDR-L1 | CDR-L2 | CDR-L3 | 18-20 | Protein |

DESCRIPTION OF EMBODIMENTS

In general, the present invention provides mouse antibody or antigen-binding fragment thereof that specifically binds PD-L1.

In one aspect, the invention provides an mouse antibody or antigen-binding fragment which specifically binds human PD-L1, and comprising nucleic acid sequence consisting of SEQ ID NO: 1, 3, 5 and 7.

In other aspect, the invention provides an mouse antibody or antigen-binding fragment which specifically binds human PD-L1, and comprising amino acid sequence consisting of SEQ ID NO: 2, 4, 6 and 8.

In another aspect, the invention provides an mouse antibody or antigen-binding fragment which specifically binds human PD-L1, and comprising a heavy chain variable region (H-CVR) selected from the group consisting of SEQ ID NOs: 9-11 (H-CDR1, H-CDR2 and H-CDR3) and its variant; and/or a light chain variable region (L-CVR) selected from the group consisting of SEQ ID NOs: 12-14 (L-CDR1, L-CDR2 and L-CDR3) or its variant.

In other aspect, the invention provides an mouse antibody or antigen-binding fragments which specifically binds human PD-L1, and comprising a heavy chain variable region (H-CVR) selected from the group consisting of SEQ ID NOs: 15-17 (H-CDR1, H-CDR2 and H-CDR3) and its variant; and/or a light chain variable region (L-CVR) selected from the group consisting of SEQ ID NOs: 18-20 (L-CDR1, L-CDR2 and L-CDR3) or its variant.

Preferably, the mouse anti-PD-L1 antibodies of the invention are selected from Q106 and Q107.

In a preferred embodiments, the present invention provides an anti-PD-L1 antibodies or antigen-binding fragments which are claimed as mouse antibodies or fragments.

In a further preferred embodiments, the present invention provides an mouse antibodies or fragments which comprise a heavy chain variable region (H-CVR) further containing mouse IgG or its variant with heavy chain FR region.

In a further preferred embodiments, the present invention provides an mouse antibodies or fragments which further contain mouse IgG$_K$ or its variant with light chain constant region.

In a preferred embodiments, the present invention provides an mouse antibodies or fragments which comprise a light chain variable region (L-CVR) further containing mouse A chain or its variant with light chain FR region.

In a preferred embodiments, the present invention provides an anti-PD-L1 antibodies or antigen-binding fragments which comprise chimeric antibody or fragments.

In a further preferred embodiments, the present invention provides an chimeric antibody or fragments which further contain mouse IgG1, IgG2a, IgG2b, IgG4 and/or a variant with heavy chain FR region.

In one aspect, the invention features an isolated antibody that specifically binds to PD-L1. In some embodiments, the antibody comprises the following variable regions (CDRs): H-CDR-1, H-CDR2 and H-CDR3. In some embodiments, the antibody further comprises the following heavy chain domain framework regions (FRs): FR-H1, FR-H2, FR-H3 and FR-H4, In some embodiments, the antibody further comprises the following CDRs: CDR-L1, CDR-L2, and CDR-L3. In some embodiments, the antibody further comprises the following light chain variable domain framework regions (FRs): FR-L1, FR-L2, FR-L3, and FR-L4.

In some embodiments, the antibody comprises (a) a V$_H$ sequence having at least 95% sequence identity; (b) a V$_L$ sequence having at least 95% sequence identity; or (c) a V$_H$ sequence as in (a) and a V$_L$ sequence as in (b).

In another aspect, the invention features an isolated antibody that competes for binding to PD-L1 with any one of the preceding antibodies. In another aspect, the invention features an isolated antibody that binds to the same epitope as any one of the preceding antibodies. In some embodiments, any one of the preceding antibodies can be an antibody fragment that specifically binds to PD-L1.

In some embodiments, the antibody fragment is selected from the group consisting of Fab, single chain variable fragment (scFv), Fv, Fab', Fab'-SH, F(ab')$_2$, and diabody.

Disclosed are anti-PD-L1 antibody, or antigen binding fragment that specifically binds to an epitope within the extracellular domain of human or mouse PD-L1, wherein the antibody comprises a full nucleic acid sequences of: SEQ ID NO:1, SEQ ID NO:3, SEQ ID NO:5, SEQ ID NO:7, SEQ ID NO:2, SEQ ID NO:4, SEQ ID NO:6, and SEQ ID NO:8. In some aspects, the antibody or fragment comprises a heavy chain variable region (HCVR) having complementarity determining regions (CDRs) selected from the group consisting of: CDRs 1-3 of SEQ ID NO: 9; CDRs 1-3 of SEQ ID NO: 10; CDRs 1-3 of SEQ ID NO: 11; CDRs 1-3 of SEQ ID NO: 15; CDRs 1-3 of SEQ ID NO: 16; CDRs 1-3 of SEQ ID NO: 17. In some aspects, the antibody or fragment, comprising a heavy chain complementarity determining regions (H-CDR) selected from the group consisting of SEQ ID NOs: 9-11 and 15-17. In some aspects, the antibody or fragment comprises a light chain variable region (LCVR) having complementarity determining regions (CDRs) selected from the group consisting of: CDRs 1-3 of SEQ ID NO: 12; CDRs 1-3 of SEQ ID NO: 13; CDRs 1-3 of SEQ ID NO: 14; CDRs 1-3 of SEQ ID NO: 18; CDRs 1-3 of SEQ ID NO: 19; CDRs 1-3 of SEQ ID NO: 20. In some aspects, antibody or fragment, comprising a light chain complementarity determining regions (L-CDR) selected from the group consisting of SEQ ID NOs: 12-14 and 18-20 and can be combined with any of the disclosed H-CDRs.

In another aspect, the present invention provides an isolated nucleic acid or DNA molecule that encodes any of the antibodies described herein.

In a further aspect, the present invention provides an isolated polynucleotide composition, comprising the anti-PD-L1 antibody light chain or a functional fragment of the polynucleotide and the anti-PD-L1 polynucleotide of the heavy chain of an antibody or functional fragment thereof.

In another aspect, the invention features an bispecific molecule of anti-PD-L1 antibodies or antigen-binding thereof of the bispecific molecule. Antibody or antigen binding portion of the invention can be derivatized or linked to another functional molecule, e.g., another peptide or protein (e.g., another antibody or ligand receptor) to generate at least two different the bispecific binding molecule binding sites or target molecules. Antibodies of the invention can in fact be derivatized or linked to more than one other functional molecule to generate more than two different binding sites and/or target molecule binding multispecific molecule; such multispecific molecules are also intended to be as used herein.

In some particular embodiments, according to the anti-PD-L1 antibody or functional fragment thereof of the present invention block the interaction and/or interact with PD-1 and PD-L2 and/or the PD-L1 and CD80.

In a further aspect, the present invention provides the use according to the anti-PD-L1 antibody or a functional fragment of the present invention in the manufacture of a medicament for enhancing the immune response of T cells. In some embodiments, the enhanced immune response includes enhancement of T cell proliferation.

In some particular embodiments, wherein the PD-L1 antibody induces tumor cell killing by executing cytolytic activity through a complement dependent cytotoxicity (CDC).

In some particular embodiments, wherein the PD-L1 antibody exhibits anti-tumor activity by having increased antibody dependent cell-mediated cytotoxicity (ADCC).

In some particular embodiments, wherein the PD-L1 antibody further kills tumor cells in NSG myeloma mice through a cytotoxic T lymphocyte (CTL) and increases its survive rate.

In some particular embodiments, wherein the PD-L1 antibody combined with chemotherapeutic drug, lenalidomide further kills myeloma cells in SCID myeloma mice and increases its survive rate.

In another aspect, the present invention provides the use according to the anti-PD-L1 antibody or a functional fragment of the present invention for the treatment or prevention of cancer and most preferably myeloma and lymphoma or infectious diseases of the medicament.

The present invention further provides a method of treating and preventing PD-L1 mediated disease or disorder, according to PD-L1 antibody or a functional fragment of the present invention or combined therapy comprising pharmaceutical compositions thereof; preferably wherein said disease is cancer, most preferably the myeloma, lymphoma; and breast cancer, prostate cancer, lung cancer, stomach cancer, colon cancer, kidney cancer, melanoma, Non-small cell lung cancer.

EXAMPLES

The invention provides novel antibodies that bind to PD-L1. Antibodies of the invention are useful, for example, for cancer treatment by blocking PD-1/PD-L1 pathway using this novel anti-PD-L1 antibody.

The following examples are provided to further explain and demonstrate some of the presently preferred embodiments and are not intended to limit the scope or content of the invention in any way.

Example-1: Generation of Anti-PD-L1 Mouse Antibodies

Anti-PD-L1 mouse monoclonal antibodies were generated by hybridoma techniques. Briefly, The DNA sequence encoding the human PD-L1 was expressed with the Fc region of mouse IgG1 at the C-terminus in human 293T cells. Balb/c mice were immunized with the purified PD-L1 antigen emulsified with complete Freund's adjuvant followed by boosting a series of PD-L1 antigen emulsified with incomplete Freund's adjuvant. The antibody-expressing fusioned cells were screened by Enzyme-Linked Immuno-abSorbant Assay (ELISA) using the coated PD-L1 antigen. All ELISA positive clones producing the antibody with the highest specificity were further selected. Two anti-PD-L1 monoclonal antibodies named as Q106 and Q107 among them were finally chosen and further produced using in serum-free medium by in vitro cell culture method, and subsequently purified by Protein A affinity chromatography.

Example-2: Screen of Anti-PD-L1 Mouse Antibodies by ELISA

Screen of anti-PD-L1 antibodies against recombinant human PD-L1 was measured by indirect ELISA assay. Ninety-six well Falcon 3912 polyvinylchloride microtiter plates (Becton Dickinson Inc, Oxnard, Calif.) were coated with 100 µL of recombinant human PD-L1-Fc at 4° C. overnight. The plate was washed three times in PBST (PBS with 0.05% Tween-20), and then blocked with PBS containing 4% BSA to prevent nonspecific binding. 100 µL of hybridoma supernatant was added to each well and incubated at room temperature for 2 hours. Wells were washed three times with PBST and 100 µL of HPR-conjugated goat anti-mouse secondary antibody (Biolegend, cat #405306) was added, and further incubated for 2 hours at room temperature. After washing, o-Phenylenediamine dihydrochloride (OPD) peroxidase substrate was added to each well and plates were incubated for 20 minutes at room temperature. Reactions were stopped using 0.36 N $H_2SO_4$ and the optical density read by an ELISA plate reader (VersaMax, Molecular Devices, Sunnyvale, Calif., USA) at a wavelength of 490 nm. The wells filled with anti-PD-L1 serum were served as the positive control. 45 positive clones were totally obtained, and continuously passaged by limited dilution of cloning. The step was repeated three times for got a stable single of hybridoma. Results showed that two positive clones Q106 and Q107 with the highest titers can stably secrete monoclonal antibodies against human PD-L1.

Example-3: Specificity of Anti-PD-L1 Antibodies

This example shows the specificity for the anti-PD-L1 antibody of the invention for human PD-L1. In addition, it shows the affinity of two antibodies Q106 and Q107 for human PD-L1 expressed at the cell membrane on 293T- transfected cells (FIG. 1A). Human PD-L1 were stably transfected into 293T cells. Cells were harvested and plated at 150,000 cells per well in a 96-well plate for binding assay. The PD-L1 antibodies Q106, Q107 or Isotype antibody control were titrated starting at 10 µg/ml, in a serial of three-fold dilutions and bound to cells in 50 µl volumes for 25 minutes on ice. Cells were washed and then detected with anti-mouse IgG PE (BD Biosciences) at 20 µg/ml for 25 minutes on ice.

All samples were run on a MiltenyiBiotech MACSQuant and Mean Fluorescence Intensity of PD-L1 binding data as a function of anti-PD-L1 antibody concentration was analyzed using FlowJo® software provided by Tree Star. $EC_{50}$ values (antibodies concentration associated with an half-maximal binding) were calculated using Kaleidagraph. These values are summarized below in Table 1:

Flow cytometry analysis also shows that the specificity of PD-L1 antibodies Q106 and Q107 in wildtype and PD-L1 knockdown mantle cell lymphoma cell line, Granta519 (FIG. 1B), and multiple myeloma cell line U266 (FIG. 1C).

Example-4: Cell Surface Bindings of Anti-PD-L1 Antibodies in Different Cancer Cell Lines Affinity purified both Q106 and Q107 antibodies in Example 1 were conjugated to the fluorochromes PE (Invitrogen). Human myeloma, breast cancer and prostate cancer cell lines were maintained in RPMI-1640 medium (Fisher Scientific, Herndon, Va.) supplemented with 10% fetal bovine serum (Atlanta Biologicals, Lawrenceville, Ga.). Cells were centrifuged and washed with PBS, then separately stained with PE-conjugated Q106 and Q107 antibodies, incubated for 30 min on ice, and washed 3 times before analysis. Flow cytometry data were collected with a FACSCantoII (Becton Dickinson) and analyzed with FlowJo V.9.1 software (TreeStar). Both Q106 and Q107 PD-L1 antibodies can bind to the cellular PD-L1 protein of Human myeloma cell lines (ARH-77 and U266), breast cancer cell lines (MB-231 and MCF-7), and prostate cancer cell lines (PC-3 and LN3) in FACS assays (FIG. 2).

Example-5: Enhancement of T Cell Proliferation in Vitro by Anti-PD-L1 Antibodies Allogeneic $CD3^+$, $CD4^+$ and $CD8^+$ T cells were purified from PBMCs from healthy donors using magnetic cell sorting (Miltenyi Biotec). $CD3^+$ T cells were labeled with 5(6)-carboxyfluorescein diacetate succinimidyl ester (CFSE; 5 □M; Invitrogen) for 10 minutes at 37° C. After washing, T cells ($5\times10^4$/100 µL/well) were seeded into 96-well U-bottomed tissue culture plates (Corning Glassworks) and cocultured with irradiated MM cell line ARH-77 at 37° C. for 6-10 days in 5% $CO_2$ in Aim-V medium supplemented with 10% pooled human serum (T-cell medium). Flow cytometry analysis was used to detect dilution of CFSE. Anti-PD-L1 antibodies Q106 and Q107 can significantly increase $CD3^+$ (FIG. 3A), $CD4^+$ (FIG. 3B) and $CD8^+$ (FIG. 3C) T cell proliferations in CFSE dilution assay.

Example-6: Enhancement of CTLs Killing Activity in Vitro by Anti-PD-L1 Antibodies A. Generation of Tumor-Reactive, Alloantigen-Specific Cytotoxic T Lymphocyte Lines Allogeneic $CD3^+$ T cells were cocultured in T-cell medium with irradiated ARH-77. After 7 days of coculture, $CD3^+$ T cells were harvested and restimulated with newly irradiated above described tumor cells. The cultures were fed with fresh T cell medium containing recombinant IL-2 (10 IU/ml), IL-7 (5 ng/ml), and IL-15 (5 ng/ml) (R&D Systems). The frequencies of $CD3^+CD8^+$ T cells were monitored every week by flow cytometry. After at least 4 repeated cycles of in vitro restimulation, cytotoxic T lymphocyte (CTL)-cell line was generated, and named as CTL-ARH-77. The CTL-cell line was expanded in T-cell medium containing recombinant IL-2 (10 IU/ml), IL-7 (5 ng/ml), and IL-15 (5 ng/ml) for 2 weeks and subjected to functional tests.

B. Cytotoxicity Assay

The standard 4-hour $^{51}$Cr-release assay was performed to measure cytolytic activity of the T-cell line with target cells including ARH-77, U266, ARP-1, K562, B cells, PBMCs and primary tumor cells isolated from multiple myeloma patients. To determine whether the cytolytic activity was restricted by Major Histocompatibility Complex (MHC) class I or II molecules, target cells were pretreated with 20 µg/ml antibodies against HLA-ABC (Serotec Ltd), HLA-DR (Immunotech), or control IgG (eBioscience).

ARH-77-reactive CTL-cell line from HLA-A*0201$^+$ healthy blood donors was generated as described above. As shown in FIG. 4A, the percentages of tumor-reactive $CD8^+$ T cells in CTL line were increased while applied Q106 antibody in CFSE dilution assay. Next, the cytolytic activity of ARH-77 CTL cell line was examined. The data showed that the CTL cells not only killed the stimulatory ARH-77 cell lines, but also killed HLA-A*0201$^+$U266 and primary MM cells (patients 1 and 2). No killing was observed on HLA-A*0201$^-$ARP-1, ARK and primary MM cells (patient 3 and 4) or K562 cells (FIG. 4B) at all, indicating that NK cells were not responsible for the killing. Moreover, purified normal allogeneic (to the T cells) PBMCs and B cells from a HLA-A*0201$^+$ donor and a MM patient were used as target cells to demonstrate whether the CTL cells were cytolytic to normal cells. As shown in FIG. 4B, no killing was observed against normal B cells or PBMCs, although the T cells were alloantigen-specific.

More importantly, when MM passaged cell lines or MM primary cells were pre-incubated with anti-PD-L1 antibodies, Q106 and Q107, respectively, these cells became more sensitive to the killing (FIG. 4B; $P<0.05$ to $P<0.01$).

Example-7: Tumor Cells Killed Through ADCC Induced by Anti-PD-L1 Antibodies

ADCC was measured by 51-Chromium (51-Cr) release assays. In ADCC assay, purified PBMCs from normal volunteers was used as effector cells. Target cells ($1\times10^6$) were incubated with 200 µCi of 51-Cr for 1 h at 37° C. with gentle resuspension of pellet at 15 min intervals. After washing, cells were plated at 10,000 cells/well in 96-well U-bottom plate with a different concentration of PBMCs. This is followed by the addition of antibody solution in a final concentration ranging from 5 to 20 µg/ml. Both anti-PD-L1 antibodies, Q106 and Q107 and mouse IgG1 (BioLegend) were used as tested groups and isotype control. Cells are then incubated for 4 h at 37° C., and released 51-Cr was analyzed using a Gamma Counter. Spontaneous release was determined from target cells without the addition of antibody and PBMCs, and maximum release was determined from target cells with 6% Triton X-100 without the addition of antibody and PBMCs. Percent cytotoxicity was calculated as [(counts in sample–spontaneous release)/(maximum counts–spontaneous release)]×100%. All experiments were performed in triplicates. Data showed that ADCC induced by anti-PD-L1 antibodies, Q106 and Q107 killed hematological tumor cells (FIG. 5A) and solid cancer cells (FIG. 5B).

Example-8: Tumor Cells Killed Through CDC Induced by Anti-PD-L1 Antibodies

CDC was measured by 51-Chromium (51-Cr) release assays as demonstrated in Example 7. In CDC assay, guinea pig serum (Sigma-Aldrich) was used as complement source. Target cells ($1\times10^6$) were incubated with 200 μCi of 51Cr for 1 h at 37° C. with gentle resuspension of pellet at 15 min intervals. After washing, cells were plated at 10,000 cells/well in 96-well U-bottom plate with different concentration of guinea pig serum. This is followed by the addition of antibody solution, in a final concentration ranging from 5 to 20 μg/ml. Both Q106 and Q107 PD-L1 antibodies and mouse IgG1 (BioLegend) were used as tested group and isotype control. Cells are then incubated for 4 h at 37° C., and released 51-Cr was analyzed using a Gamma Counter. Spontaneous release was determined from target cells without the addition of antibody and guinea pig serum, and maximum release was determined from target cells with 6% Triton X-100 without the addition of antibody and guinea pig serum. Percent cytotoxicity was calculated as [(counts in sample−spontaneous release)/(maximum counts−spontaneous release)]×100%. All experiments were performed in triplicate. The data showed that CDC induced by anti-PD-L1 antibodies, Q106 and Q107 killed both hematological tumor cells (FIG. 6A) and solid cancer cells (FIG. 6B).

Example-9: Immunotherapy of PD-L1 Antibody in NSG Myeloma Mouse Model

It is now apparent that many tumors exploit expression of PD-1 ligands as a means to attenuate anti-tumor T cells responses. Several human cancers have been characterized to express elevated levels of PD-L1 on both tumors and tumor-infiltrating leukocytes and this elevated PD-L1 expression is often associated with a worse prognosis. Mouse tumor models demonstrate similar increases in PD-L1 expression within tumors and demonstrate a role for the PD-1/PD-L1 pathway in inhibiting tumor immunity.

Here we present an experiment demonstrating the impact of blocking PD-L1 on multiple myeloma U266 of growth in NSG mice (FIGS. 7A and 7B). These cells express PD-L1, but not PD-L2 on their cell surface as assessed by Flow Cytometry. Mice were inoculated intravenously with 1 million U266 cells on Day 0. On Day 14 (when tumors were seen in luminous image), 10 mice/group were treated with 10 mg/kg of PD-L1 antibody (Q106) for the 3×/week duration of the study. In the study, mouse IgG was set up as control. Blockade of PD-L1 in late intervention is highly effective as a single agent therapy at preventing tumor growth. In contrast, control IgG showed no evidence of inhibiting tumor growth. These results demonstrate the unique role of the PD-1/PD-L1 axis in suppression of the anti-tumor immune response and support the potential for the treatment of human cancers with the antibody that blocks the PD-L1 interaction with PD-1 and B7.1.

U266 NSG tumor model: Methodically, on Day 0, 40 of mice were inoculated intravenously with 1 million of U266-luciferase cell in 100 microliters of PBS. Take image in IVIS imaging system every week after tumor inoculation. About 2-3 weeks later, 30 of 40 mice with similar-sized tumors were recruited into one of 3 treatment groups as listed below. The tumors were measured by taking image every week. Mice not recruited into below treatment groups, due to dissimilar tumor volume were euthanized:

Group 1: PBS control, IP, 100 μL, 3×/week;

Group 2: IgG control, 10 mg/kg IP, 100 μL, 3×/week;

Group 3: anti-PD-L1 antibody Q106, 10 mg/kg IP, 100 μL, 3×/week.

Example-10: Combination Immunotherapy of PD-L1 Antibody with Lenalidomide in SCID Myeloma Mouse Model Shown are bioluminescence images (FIG. 8A), tumor burdens (FIG. 8B) and survival (FIG. 8C) of mice received a different treatments. Representative results from two independent experiments performed are shown. Error bars=SEM.*P<0.05, compared with mouse IgG control.

On Day 0, 60 of SCID mice were inoculated subcutaneously with 2 million of U266-luciferase myeloma cells in 100 microliters of PBS plus matrigel. Mice are allowed to grow tumors. Mice are weighed and measured 2×/week until Day 15 (when the tumor volume is between 100-200 mm3). On Day 15, following tumor measurement, mice are recruited into 1 of the 4 treatment groups below. Mice not recruited into below treatment groups, due to dissimilar tumor volume are euthanized.

Group 1: IgG control, 10 mg/kg IP, 100 μL, 3×/week×5, n=10;

Group 2: anti-PD-L1 antibody Q106, 10 mg/kg IP, 100 μL, 3×/week×5, n=10;

Group 3: Lenalidomide, 10 mg/kg IP, 100 μL, for 5 days and 2 days off for 3 weeks, n=10;

Group 4: anti-PD-L1 antibody Q106 +Lenalidomide, n=10.

Tumors are measured, luminous image taken and mice weighed 2×/week. Animals exhibiting weight loss of >15% will be weighed daily and euthanized if they lose >20% body weight. Mice will be euthanized when tumor volumes exceed 3,000 mm3, or after 3 months if tumors do not form.

This study showed that combination immunotherapy of anti-PD-L1 antibody, Q106 with lenalidomide blockade was more effective than treatment with the PD-L1 antibody or lenalidomide chemotherapy alone (FIGS. 8A-C).

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

TABLE 1

| $EC_{50}$ Summary | |
| --- | --- |
| mAbs | $EC_{50}$ (nM) in FACS |
| Q106 | 0.3 |
| Q107 | 0.5 |

TABLE 2

DNA and Amino acid sequences of $V_H$, $V_L$ and their CDR domains

| $V_H$/$V_L$/CDR | Sequence ID for Q106 | Sequence ID for Q10711 |
|---|---|---|
| $V_H$ DNA | SEQ ID NO:1 | SEQ ID NO:5 |
| $V_H$ AA | SEQ ID NO:2 | SEQ ID NO:6 |
| $V_L$ DNA | SEQ ID NO:3 | SEQ ID NO:7 |
| $V_L$ AA | SEQ ID NO:4 | SEQ ID NO:8 |
| H-CDR1 AA | SEQ ID NO:9 | SEQ ID NO:15 |
| H-CDR2 AA | SEQ ID NO:10 | SEQ ID NO:16 |
| H-CDR3 AA | SEQ ID NO: 11 | SEQ ID NO:17 |
| L-CDR1 AA | SEQ ID NO:12 | SEQ ID NO:18 |
| L-CDR2 AA | SEQ ID NO:13 | SEQ ID NO:19 |
| L-CDR3 AA | SEQ ID NO:14 | SEQ ID NO:20 |

REFERENCE TO DEPOSITED BIOLOGICAL MATERIAL

Not apply in this application.

SEQUENCE LISTING FREE TEXT

SEE SEQUENCE LISTING FILE-RUNSHIN

PATENT LITERATURE

PTL1: WO2013173223A1
PTL2: WO2007005874A2
PTL3: WO2010077634A1
PTL4: WO2011066342A2
PTL5: WO2011066389A1
PTL6: WO2014100079A1
PTL7: U.S. Pat. No. 8,217,149

NON PATENT LITERATURE

NPL1: Julie R. Brahmer, Scott S. Tykodi, Laura Q. M. Chow, Safety and Activity of Anti-PD-L1 Antibody in Patients with Advanced Cancer N Engl J Med. 2012; 366 (26):2455-65.

NPL2: Webster R M. The immune checkpoint inhibitors: where are we now? Nat Rev Drug Discov. 2014; 13(12): 883-4.

NPL3: Keir M E, Butte M J, Freeman G J, Sharpe A H. PD-1 and its ligands in tolerance and immunity. Annu Rev Immunol. 2008; 26:677-704.

NPL4: Velcheti V, Schalper K A, Carvajal D E, et al. Programmed death ligand-1 expression in non-small cell lung cancer. Lab Invest. 2014; 94:107-16.

NPL5: Christophe Massard, Michael S. Gordon, Sunil Sharma, Safety and Efficacy of Durvalumab (MEDI4736), an Anti-Programmed Cell Death Ligand-1 Immune Checkpoint Inhibitor, in Patients With Advanced Urothelial Bladder Cancer, J Clin Oncol, 2016, 34, 9761.

NPL6: Powles T, Eder J P, Fine G D, et al: MPDL3280A (anti-PD-L1) treatment leads to clinical activity in metastatic bladder cancer. Nature, 2014, 515:558-562.

BRIEF DESCRIPTION OF DRAWINGS

The invention can be more completely understood with reference to the following drawings.

SEQUENCE LISTING

Figure 1A:
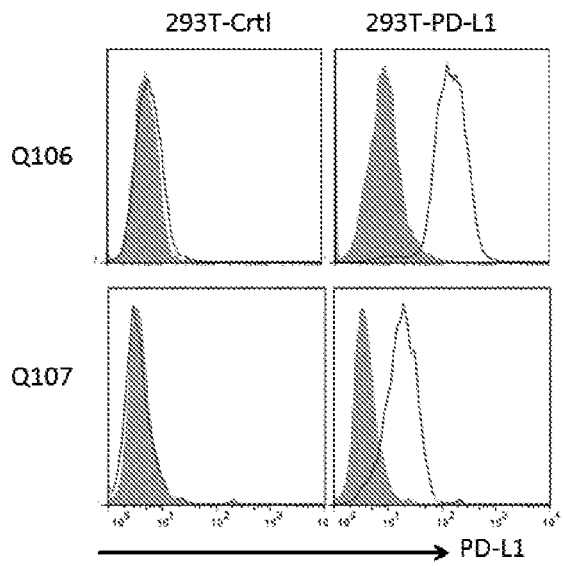
FIG. 1a Flow cytometry analysis shows binding specificity of anti-PD-L1 antibodies Q106 and Q107 in wildtype and PD-L1-expressing 293T cell lines.
Figure 1B:
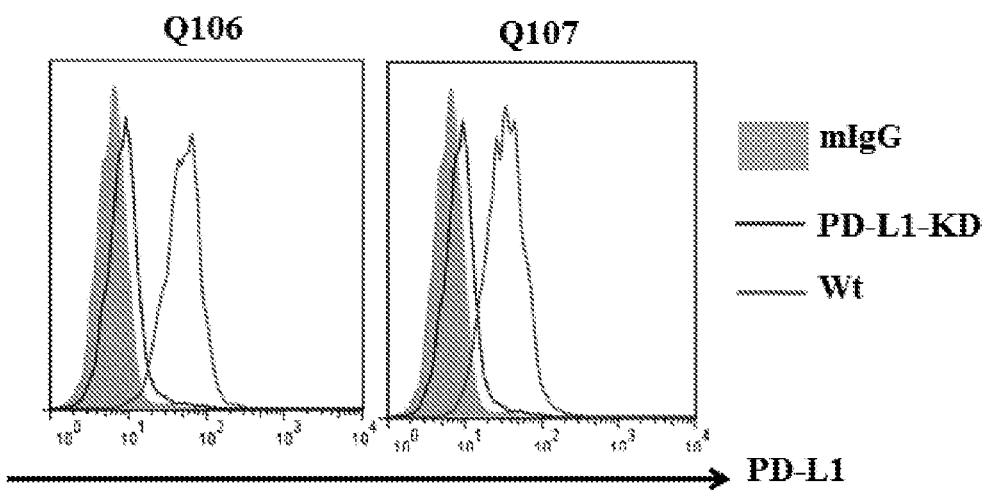
FIG. 1b Flow cytometry analysis shows binding specificity of anti-PD-L1 antibodies Q106 and Q107 in wildtype and PD-L1 knockdown mantle cell lymphoma cell lines.
Figure 1C:
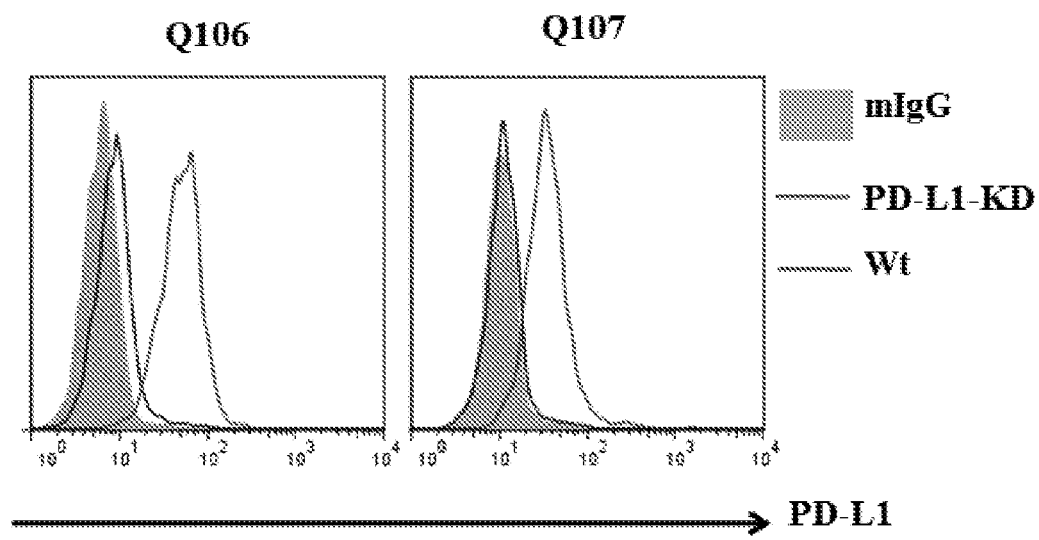
FIG. 1c Flow cytometry analysis shows cell surface binding specificity of anti-PD-L1 antibodies Q106 and Q107 in wildtype and PD-L1 knockdown multiple myeloma cell lines.
Figure 2:
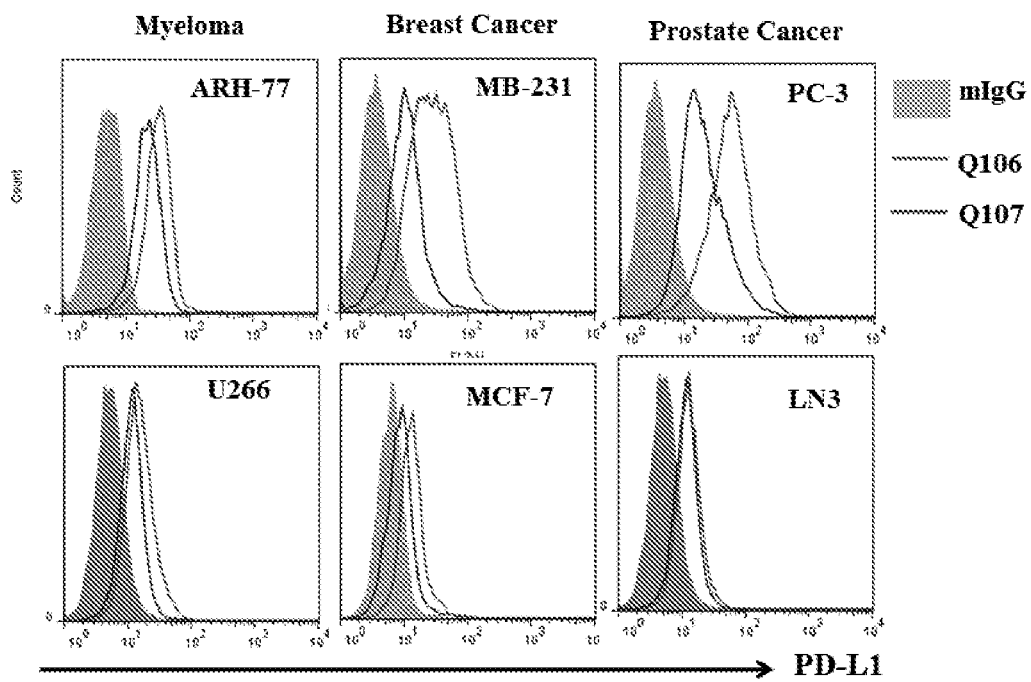
FIG. 2 Flow cytometry analysis shows cellular binding of anti-PD-L1 antibodies Q106 and Q107 in a different cancer cell lines.
Figure 3A:
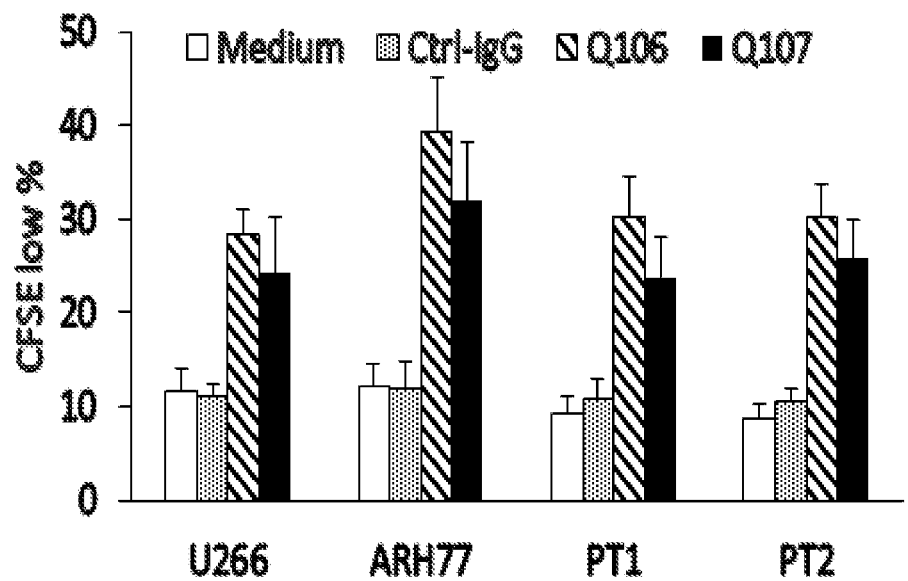
FIG. 3a Anti-PD-L1 antibodies Q106 and Q107 increase $CD3^+$ T cell proliferation in CFSE dilution assay.
Figure 3B:
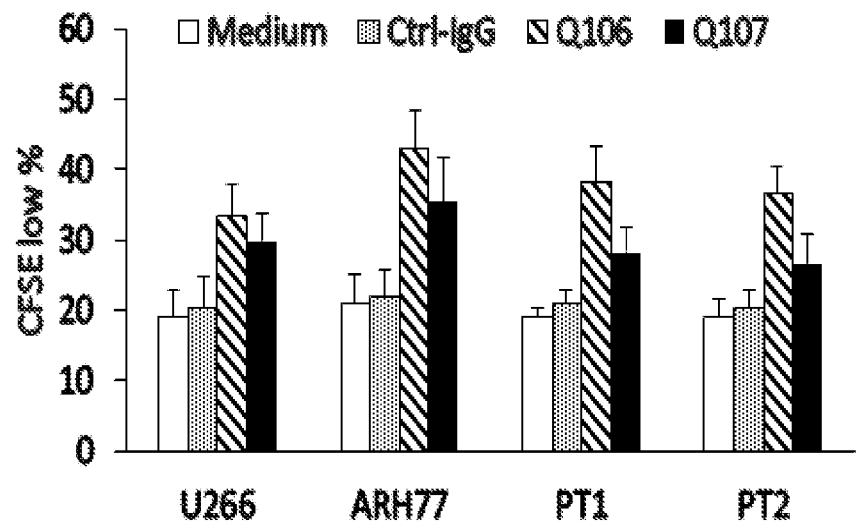
FIG. 3b Anti-PD-L1 antibodies Q106 and Q107 increase $CD4^+$ T cell proliferation in CFSE dilution assay.
Figure 3C:
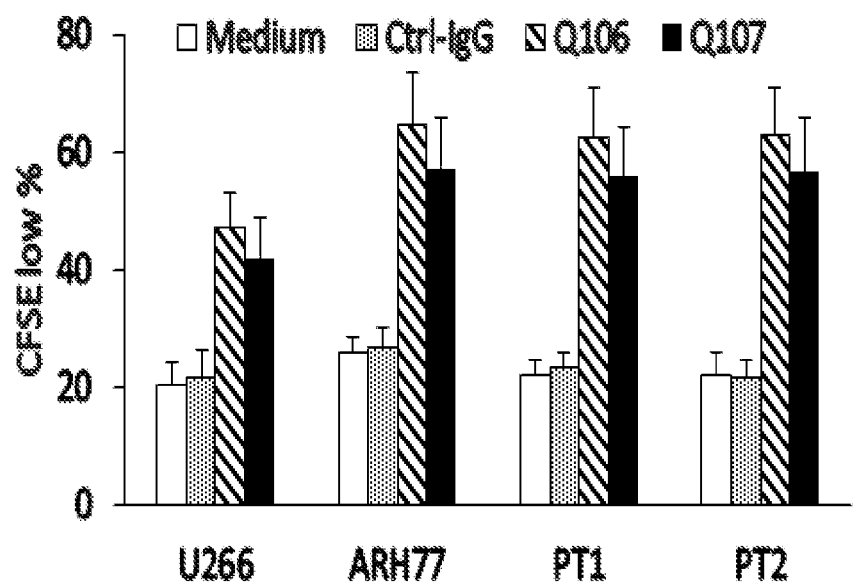
FIG. 3c Anti-PD-L1 antibodies Q106 and Q107 increase $CD8^+$ T cell proliferation in CFSE dilution assay.
Figure 4A:
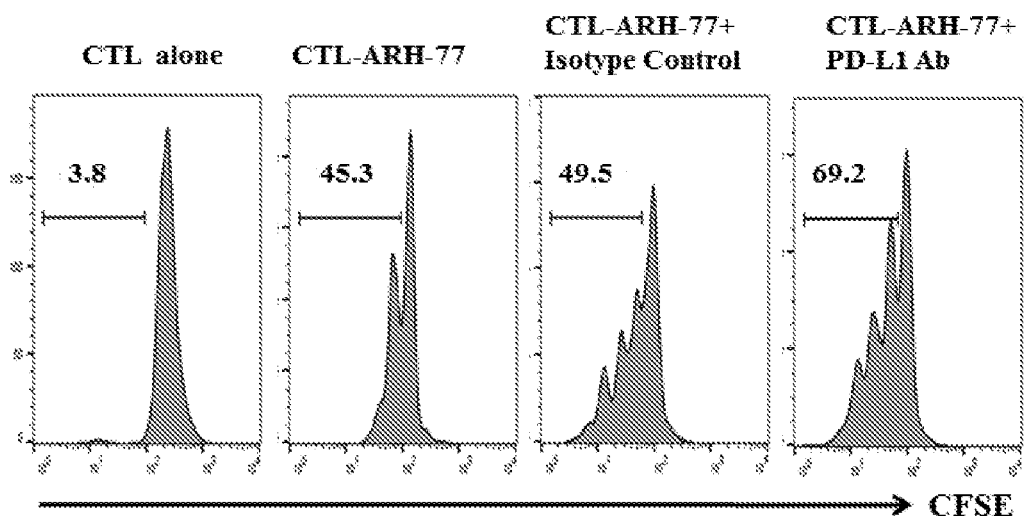
FIG. 4a Anti-PD-L1 antibody Q106 enhances CTL cells proliferation in CFSE dilution assay.
Figure 4B:
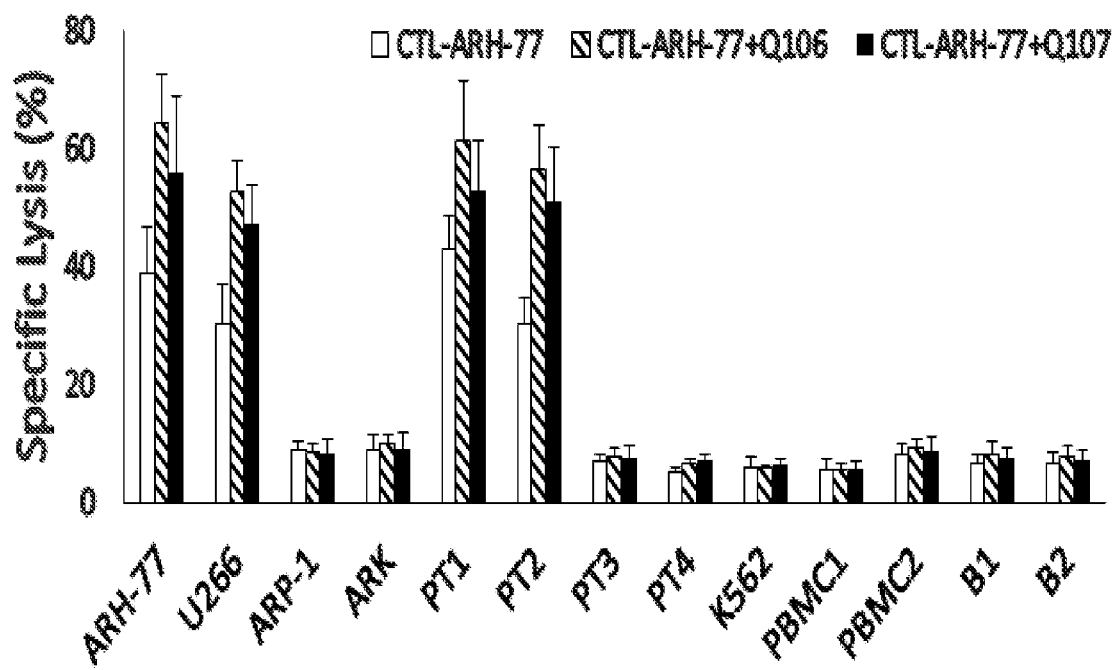
FIG. 4b Anti-PD-L1 antibodies Q106 and Q107 kill cancer cells by enhanced CTLs in $^{51}Cr$ cytotoxicity assay.
Figure 5A:
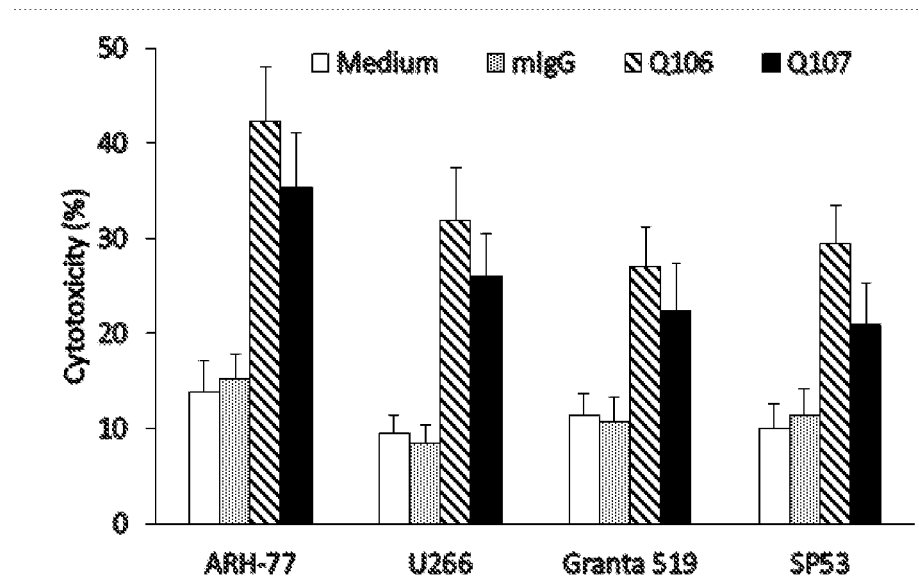
FIG. 5a Anti-PD-L1 antibodies Q106 and Q107 kill hematological tumor cells by induced ADCC.
Figure 5B:
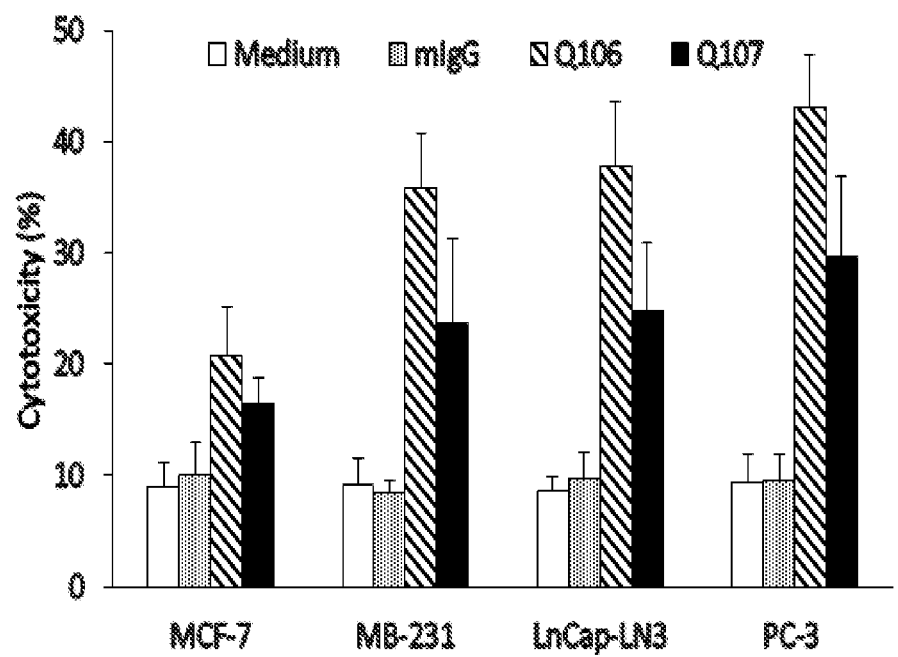
FIG. 5b Anti-PD-L1 antibodies Q106 and Q107 kill solid cancer cells by induced ADCC.
Figure 6A:
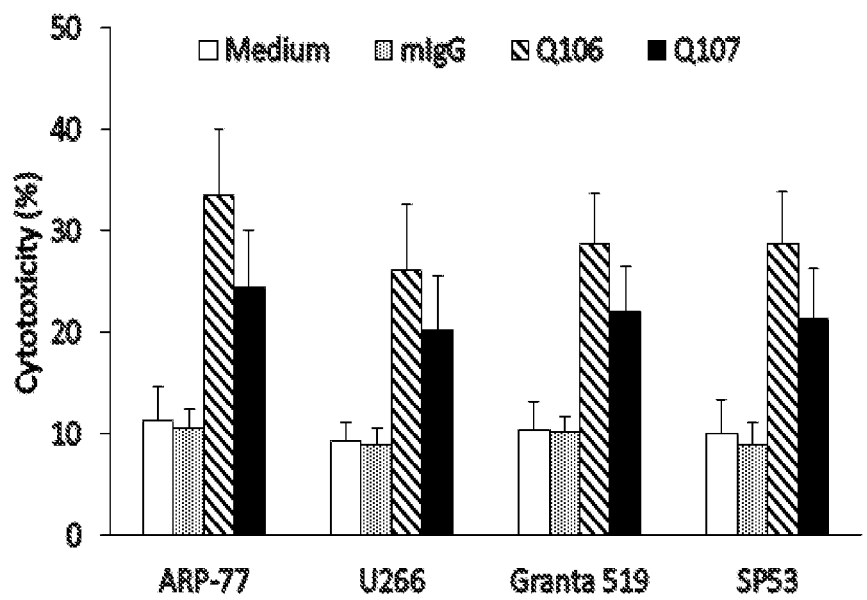
FIG. 6a Anti-PD-L1 antibodies Q106 and Q107 kill hematological tumor cells by induced CDC.
Figure 6B:
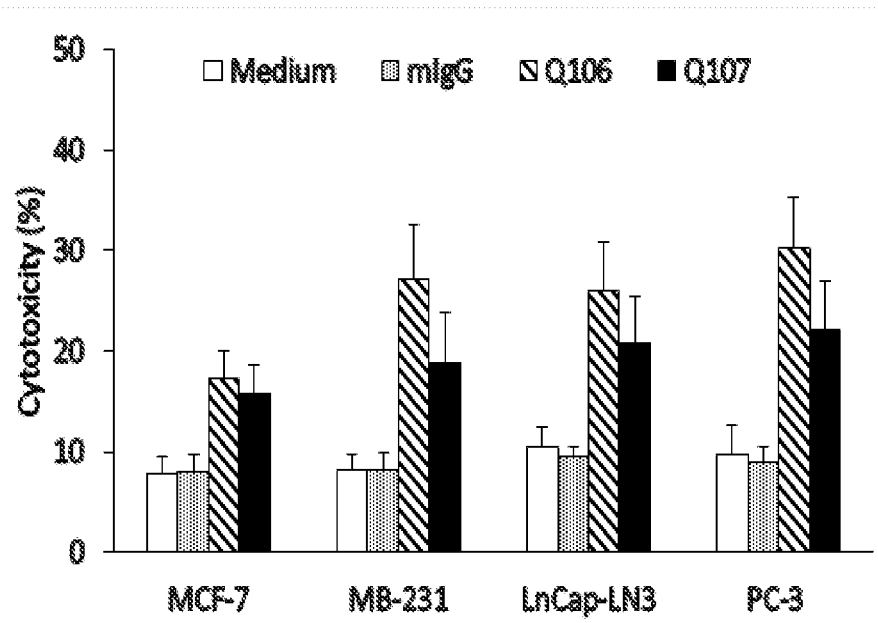
FIG. 6b Anti-PD-L1 antibodies Q106 and Q107 kill solid cancer cells by induced CDC.
Figure 7A:
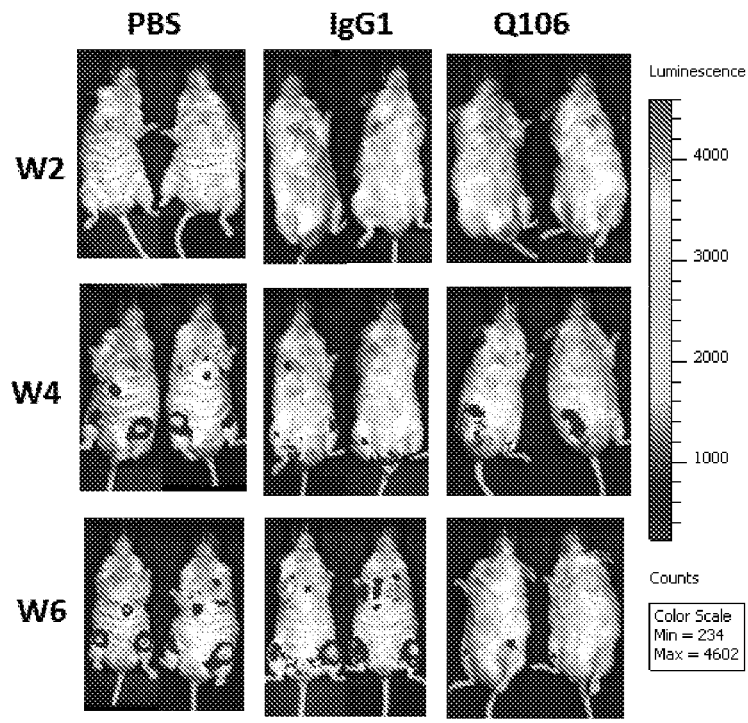
FIG. 7a Immunotherapy of PD-L1 antibody Q106 in NSG myeloma mouse model.
Figure 7B:
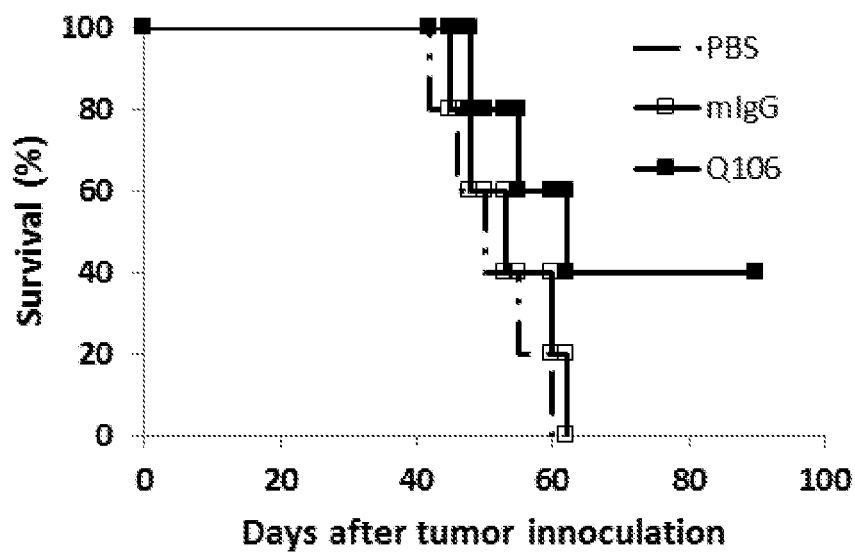
FIG. 7b Survival curve of immunotherapy of PD-L1 antibody Q106 in NSG myeloma mouse model.
Figure 8A:
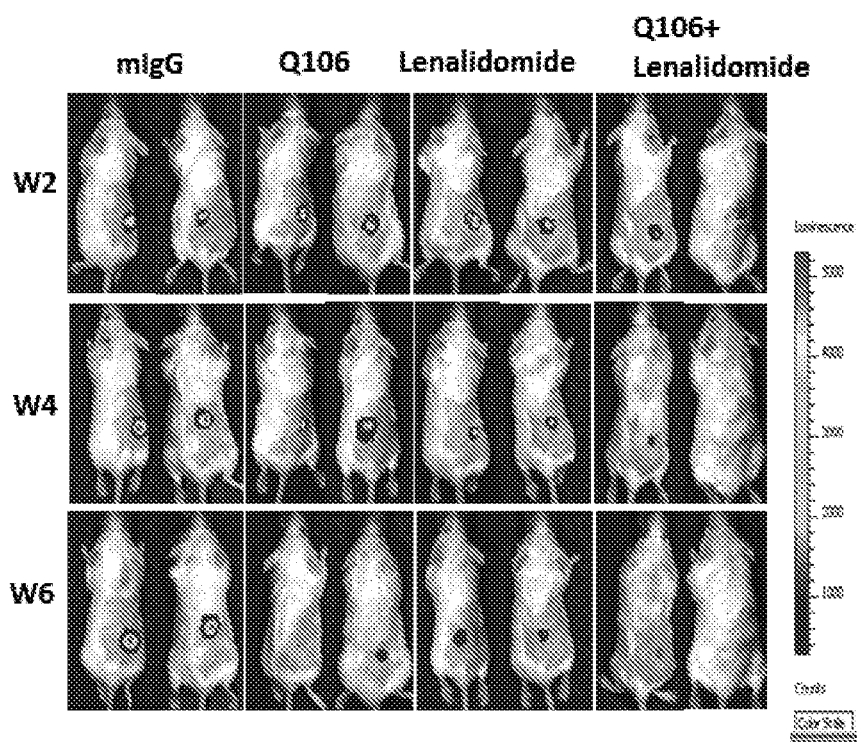
FIG. 8a Combination immunotherapy of PD-L1 antibody Q106 with lenalidomide in SCID myeloma mouse model.
Figure 8B:
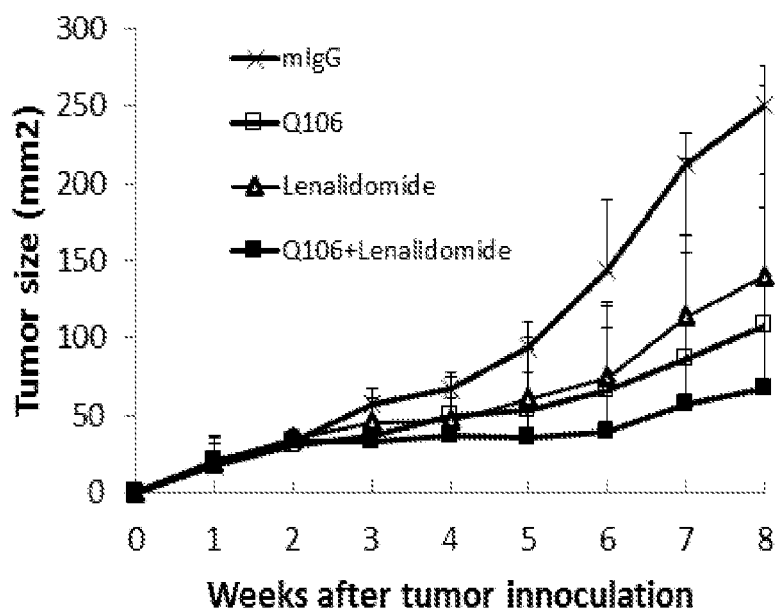
FIG. 8b Combination immunotherapy of PD-L1 antibody Q106 with lenalidomide Inhibits tumor growth in SCID myeloma mouse model.
Figure 8C:
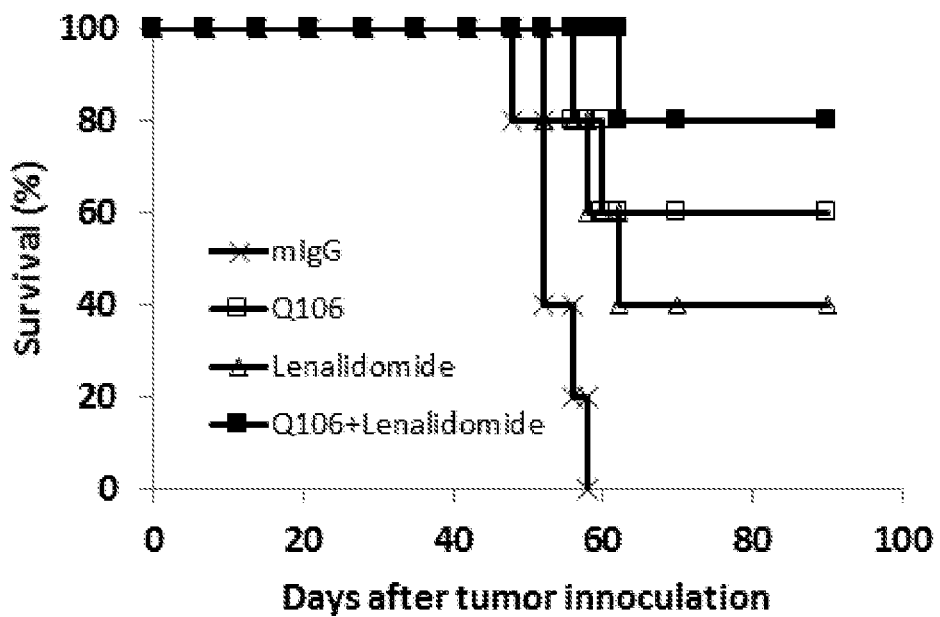
FIG. 8c Combination immunotherapy of PD-L1 antibody Q106 with lenalidomide enhances survival rate in SCID myeloma mouse model.

```
<160> NUMBER OF SEQ ID NOS: 20

<210> SEQ ID NO 1
<211> LENGTH: 360
<212> TYPE: DNA
<213> ORGANISM: Mouse

<400> SEQUENCE: 1
tctgatgtgc agcttcagga gtcgggacct ggcctggtga aaccttctca gtctctgtcc    60
```

```
ctcacctgct ctgtcactgg ctactctatc accagtgatt atgcctggaa ctggatccgg    120
cagtttccag agacacact  ggagtggatg ggctacataa actacagtgg tagctctacc    180
tacaacccat ctctcataag tcgactctct atcactcgag acacatccaa gaaccagttc    240
ttcctgcagt tgaattctgt gacttctgag gacacagcca catattactg tgcaagaggc    300
cctgactggg actggtactt tgactactgg ggccaaggca ccactctcac agtctcctca    360
```

<210> SEQ ID NO 2
<211> LENGTH: 120
<212> TYPE: PRT
<213> ORGANISM: Mouse

<400> SEQUENCE: 2

```
Ser Asp Val Gln Leu Gln Glu Ser Gly Pro Gly Leu Val Lys Pro Ser
1               5                   10                  15

Gln Ser Leu Ser Leu Thr Cys Ser Val Thr Gly Tyr Ser Ile Thr Ser
            20                  25                  30

Asp Tyr Ala Trp Asn Trp Ile Arg Gln Phe Pro Gly Asp Thr Leu Glu
        35                  40                  45

Trp Met Gly Tyr Ile Asn Tyr Ser Gly Ser Ser Thr Tyr Asn Pro Ser
    50                  55                  60

Leu Ile Ser Arg Leu Ser Ile Thr Arg Asp Thr Ser Lys Asn Gln Phe
65                  70                  75                  80

Phe Leu Gln Leu Asn Ser Val Thr Ser Glu Asp Thr Ala Thr Tyr Tyr
                85                  90                  95

Cys Ala Arg Gly Pro Asp Trp Asp Trp Tyr Phe Asp Tyr Trp Gly Gln
            100                 105                 110

Gly Thr Thr Leu Thr Val Ser Ser
        115                 120
```

<210> SEQ ID NO 3
<211> LENGTH: 318
<212> TYPE: DNA
<213> ORGANISM: Mouse

<400> SEQUENCE: 3

```
gatattgtgc taactcagtc tccagccacc ctgtctgtga ctccaggaga tagcgtcagt    60
ctttcctgca gggccagcca aagtattagc aacaacctac actggtatca acaaaaatca    120
catgagtctc caaggcttct catcaagtac gcttcccagt ccatctctgg gatcccctcc    180
aggttcagtg gcagtggatc agggaccgat ttcactctca gtatcaacgg tgtggagact    240 gaagatttg  gaatgtattt ctgtcaacag actaacagct ggccgacgtt cggtggaggc    300
accaaactgg aaatcaaa                                                 318
```

<210> SEQ ID NO 4
<211> LENGTH: 106
<212> TYPE: PRT
<213> ORGANISM: Mouse

<400> SEQUENCE: 4

```
Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45
```

```
Lys Tyr Ala Ser Gln Ser Ile Ser Gly Ile Pro Ser Arg Phe Ser Gly
        50                  55                  60

Ser Gly Ser Gly Thr Asp Phe Thr Leu Ser Ile Asn Gly Val Glu Thr
 65                  70                  75                  80

Glu Asp Phe Gly Met Tyr Phe Cys Gln Gln Thr Asn Ser Trp Pro Thr
                 85                  90                  95

Phe Gly Gly Gly Thr Lys Leu Glu Ile Lys
            100                 105

<210> SEQ ID NO 5
<211> LENGTH: 360
<212> TYPE: DNA
<213> ORGANISM: Mouse

<400> SEQUENCE: 5
gaggatgtgc agcttcagga gtcgggacct ggcctggtga accttctca gtctctgtcc      60 ctcacctgct ctgtcactgg ctactctatc tctagtgatt atgcctggaa ctggatccgg    120
cagtttggcg agacacact ggagtggatg gctacataa actacagtgg tagctctacc     180
tacaacgggt ctctcataag tcgactctct tctactcgag acacatccaa gaaccagttc    240
ttcctgcagt tgaattctgt gacttctgag acacagcca catattactg tgcaagaggc    300
ccttcagggg actggtacaa cgactactgg ggccaaggca ccactctcac agtctcctca    360

<210> SEQ ID NO 6
<211> LENGTH: 120
<212> TYPE: PRT
<213> ORGANISM: Mouse

<400> SEQUENCE: 6

Glu Asp Val Gln Leu Gln Glu Ser Gly Pro Gly Leu Val Lys Pro Ser
 1               5                  10                  15

Gln Ser Leu Ser Leu Thr Cys Ser Val Thr Gly Tyr Ser Ile Ser Ser
                20                  25                  30

Asp Tyr Ala Trp Asn Trp Ile Arg Gln Phe Gly Gly Asp Thr Leu Glu
             35                  40                  45

Trp Met Gly Tyr Ile Asn Tyr Ser Gly Ser Ser Thr Tyr Asn Gly Ser
         50                  55                  60

Leu Ile Ser Arg Leu Ser Ser Thr Arg Asp Thr Ser Lys Asn Gln Phe
 65                  70                  75                  80

Phe Leu Gln Leu Asn Ser Val Thr Ser Glu Asp Thr Ala Thr Tyr Tyr
                 85                  90                  95

Cys Ala Arg Gly Pro Ser Gly Asp Trp Tyr Asn Asp Tyr Trp Gly Gln
            100                 105                 110

Gly Thr Thr Leu Thr Val Ser Ser
        115                 120

<210> SEQ ID NO 7
<211> LENGTH: 318
<212> TYPE: DNA
<213> ORGANISM: Mouse

<400> SEQUENCE: 7
gatattgtgc taactcagtc tccagccgac ctgtctgtga ctccaggaga tagcgtcagt     60
ctttcctgca gggccagcca agtattagc tcaaacctac actggtatca acaaaaatca    120
catgagtctc caaggcttct catcaagtac gcttcccagt ccggctctgg gatcccctcc    180
aggttcagtg gcagtggatc agggaccgat ttcactctca gtatcaacgg tgtggagact    240
```

```
gaagattttg gaatgtattt ctgtcaacag actaacattt ggggcacgtt cggtggaggc    300
accaaactgg aaatcaaa                                                  318
```

<210> SEQ ID NO 8  
<211> LENGTH: 106  
<212> TYPE: PRT  
<213> ORGANISM: Mouse
<400> SEQUENCE: 8

```
Asp Ile Val Leu Thr Gln Ser Pro Ala Asp Leu Ser Val Thr Pro Gly
1               5                   10                  15

Asp Ser Val Ser Leu Ser Cys Arg Ala Ser Gln Ser Ile Ser Ser Asn
            20                  25                  30

Leu His Trp Tyr Gln Gln Lys Ser His Glu Ser Pro Arg Leu Leu Ile
        35                  40                  45

Lys Tyr Ala Ser Gln Ser Gly Ser Gly Ile Pro Ser Arg Phe Ser Gly
    50                  55                  60

Ser Gly Ser Gly Thr Asp Phe Thr Leu Ser Ile Asn Gly Val Glu Thr
65                  70                  75                  80

Glu Asp Phe Gly Met Tyr Phe Cys Gln Gln Thr Asn Ile Trp Gly Thr
                85                  90                  95

Phe Gly Gly Gly Thr Lys Leu Glu Ile Lys
            100                 105
```

<210> SEQ ID NO 9  
<211> LENGTH: 9  
<212> TYPE: PRT  
<213> ORGANISM: Mouse
<400> SEQUENCE: 9

```
Gly Tyr Ser Ile Thr Ser Asp Tyr Ala
1               5
```

<210> SEQ ID NO 10  
<211> LENGTH: 10  
<212> TYPE: PRT  
<213> ORGANISM: Mouse
<400> SEQUENCE: 10

```
Ser Gly Ser Ser Thr Tyr Asn Pro Ser Leu
1               5                   10
```

<210> SEQ ID NO 11  
<211> LENGTH: 10  
<212> TYPE: PRT  
<213> ORGANISM: Mouse
<400> SEQUENCE: 11

```
Gly Pro Asp Trp Asp Trp Tyr Phe Asp Tyr
1               5                   10
```

<210> SEQ ID NO 12  
<211> LENGTH: 6  
<212> TYPE: PRT  
<213> ORGANISM: Mouse
<400> SEQUENCE: 12

```
Gln Ser Ile Ser Asn Asn
1               5
```

<210> SEQ ID NO 13
<211> LENGTH: 6
<212> TYPE: PRT
<213> ORGANISM: Mouse

<400> SEQUENCE: 13

Ala Ser Gln Ser Ile Ser
1               5

<210> SEQ ID NO 14
<211> LENGTH: 8
<212> TYPE: PRT
<213> ORGANISM: Mouse

<400> SEQUENCE: 14

Gln Gln Thr Asn Ser Trp Pro Thr
1               5

<210> SEQ ID NO 15
<211> LENGTH: 9
<212> TYPE: PRT
<213> ORGANISM: Mouse

<400> SEQUENCE: 15

Gly Tyr Ser Ile Ser Ser Asp Tyr Ala
1               5

<210> SEQ ID NO 16
<211> LENGTH: 10
<212> TYPE: PRT
<213> ORGANISM: Mouse

<400> SEQUENCE: 16

Ser Gly Ser Ser Thr Tyr Asn Gly Ser Leu
1               5                   10

<210> SEQ ID NO 17
<211> LENGTH: 10
<212> TYPE: PRT
<213> ORGANISM: Mouse

<400> SEQUENCE: 17

Gly Pro Ser Gly Asp Trp Tyr Asn Asp Tyr
1               5                   10

<210> SEQ ID NO 18
<211> LENGTH: 6
<212> TYPE: PRT
<213> ORGANISM: Mouse

<400> SEQUENCE: 18

Gln Ser Ile Ser Ser Asn
1               5

<210> SEQ ID NO 19
<211> LENGTH: 6
<212> TYPE: PRT
<213> ORGANISM: Mouse

<400> SEQUENCE: 19

Ala Ser Gln Ser Gly Ser
1               5

<210> SEQ ID NO 20
<211> LENGTH: 8

```
<212> TYPE: PRT
<213> ORGANISM: Mouse

<400> SEQUENCE: 20

Gln Gln Thr Asn Ile Trp Gly Thr
1               5
```

The invention claimed is:

1. An anti-PD-L1 antibody, or antigen binding fragment thereof, which comprises one of the following sets of heavy chain complementarity determining regions (HCDR) and light chain variable regions (LCDR):
   a) SEQ ID NO:9 (HCDR 1), SEQ ID NO:10 (HCDR 2), SEQ ID NO:11 (HCDR 3),
   SEQ ID NO:12 (LCDR 1), SEQ ID NO:13 (LCDR 2) and SEQ ID NO:14 (LCDR 3); or
   b) SEQ ID NO:15 (HCDR1), SEQ ID NO:16 (HCDR2), SEQ ID NO:17 (HCDR3),
   SEQ ID NO:18 (LCDR1), SEQ ID NO:19 (LCDR2) and SEQ ID NO:20 (LCDR3).

2. The anti-PD-L1 antibody, or antigen binding fragment thereof, according to claim 1, which comprises
   a) a heavy chain variable domain according to SEQ ID NO:2 and a light chain variable domain according to SEQ ID NO:4; or
   b) a heavy chain variable domain according to SEQ ID NO:6 and a light chain variable domain according to SEQ ID NO:8.

3. The anti-PD-L1 antibody, or antigen binding fragment thereof, according to claim 1, which comprises
   a) a heavy chain variable domain having at least 95% sequence identity with SEQ ID NO:2 and a light chain variable domain having at least 95% sequence identity with SEQ ID NO:4; or
   b) a heavy chain variable domain having at least 95% sequence identity with SEQ ID NO:6 and a light chain variable domain having at least 95% sequence identity with SEQ ID NO:8.

4. The anti-PD-L1 antibody, or antigen binding fragment thereof, according to claim 1, wherein the antibody is IgG1 or IgG4.

5. The anti-PD-L1 antibody, or antigen binding fragment thereof, according to claim 1, wherein the antibody is IgG1λ or IgG1κ.

6. The anti-PD-L1 antibody, or antigen binding fragment thereof, according to claim 1, wherein the antigen binding fragment is selected from the group consisting of Fab, single chain variable fragment (scFv), Fv, Fab', Fab'-SH, F(ab')2, and diabody.

7. The anti-PD-L1 antibody, or antigen binding fragment thereof, according to claim 1, wherein the antibody, or antigen binding fragment, specifically binds to an epitope within the extracellular domain of human or mouse PD-L1.

8. A method for treating or preventing a cancer or an infectious disease in a subject, which method comprises administration, to a human or animal subject, of an anti-PD-L1 antibody, or antigen binding fragment thereof, according to claim 1.

* * * * *